US00PP36496P3

(12) United States Plant Patent
Straub et al.

(10) Patent No.: US PP36,496 P3
(45) Date of Patent: Feb. 25, 2025

(54) ***CANNABIS* PLANT NAMED 'OW-1'**

(50) Latin Name: *Cannabis sativa*
Varietal Denomination: OW-1

(71) Applicants: David Straub, Willow, AK (US); Matt Gore, Wasilla, AK (US)

(72) Inventors: David Straub, Willow, AK (US); Matt Gore, Wasilla, AK (US)

( * ) Notice: Subject to any disclaimer, the term of this patent is extended or adjusted under 35 U.S.C. 154(b) by 0 days.

(21) Appl. No.: 18/445,004

(22) Filed: Feb. 27, 2023

(65) Prior Publication Data

US 2023/0337560 P1 Oct. 19, 2023

Related U.S. Application Data

(63) Continuation-in-part of application No. 17/119,082, filed on Dec. 11, 2020, now abandoned.

(60) Provisional application No. 62/947,519, filed on Dec. 12, 2019.

(51) Int. Cl.
*A01H 5/02* (2018.01)
*A01H 6/28* (2018.01)

(52) U.S. Cl.
USPC ..... Plt./258
CPC ..... *A01H 6/28* (2018.05)

(58) Field of Classification Search
USPC ..... Plt./258
CPC ..... A01H 5/02; A01H 5/12
See application file for complete search history.

(56) References Cited

U.S. PATENT DOCUMENTS

PP35,171 P2 * 5/2023 Haddad ..... A01H 6/28 Plt./258
PP35,380 P3 * 9/2023 Baasch ..... A01H 6/28 Plt./258

* cited by examiner

*Primary Examiner* — Kent L Bell
(74) *Attorney, Agent, or Firm* — Hunt IP Law

(57) ABSTRACT

The unique *Cannabis* plant *C. sativa* 'OW-1' is provided. The variety can be distinguished by its elevated levels of CBGA.

4 Drawing Sheets

Latin name of the genus and species: Genus—*Cannabis*. Species—*sativa*.

Variety denomination: The new *Cannabis* plant claimed is of the variety denominated 'OW-1'.

BACKGROUND OF THE INVENTION

Field of the Invention

The present invention relates to a new and distinct annual variety of *C. sativa* hybrid, which has been given the variety denomination of 'OW-1'. 'OW-1' is intended for use as medicinal herb, for sale in *Cannabis* dispensaries, and as a home garden plant.

Background of the Related Art

The genus *Cannabis* has been in use by humans for millennia, due to the multiplicity of its benefits to humans, including the considerable value and utility of its fiber, the nutritional value of its seeds, and the medicinal value of its floral parts and products made from them. Currently the genus is under intense legal commercialization in the United States as industrial hemp for a variety of purposes including biodegradable plastics and building materials, clothing, paper, food, fuel and medicines.

Cannabidiol (CBD) extracted from *Cannabis* is widely used in over-the-counter medicines and topical treatments and is also the active ingredient in the FDA-approved drug Epidiolex® (cannabidiol). CBD is just one of at least dozens—perhaps hundreds—of cannabinoids endogenous to *Cannabis*, tetrahydrocannabinol (THC) being the other cannabinoid that is most well-known. The cannabinoids as a group interact with the human endocannabinoid receptors, which are distributed in the brain and throughout the body. The study of the endocannabinoid system (ECS) in humans and other mammals is an area of increasing interest and holds tremendous promise for the future of medicine. See, e.g., Russo (2019). *Cannabis* and Pain, *Pain Medicine,* 20(10): 1093/pm/pnz227; and Russo (2016). Clinical Endocannabinoid Deficiency Reconsidered: Current Research Supports the Theory in Migraine, Fibromyalgia, Irritable Bowel, and Other Treatment-Resistant Syndromes, *Cannabis Cannabinoid Res.* 1(1): 154-165.

Non-hemp forms of *Cannabis*, frequently referred to as marijuana, have been legalized for medicinal use in many states and also for recreational use (sometimes called "adult use") in a growing number of states including Alaska, Arizona, California, Colorado, Illinois, Maine, Massachusetts, Michigan, Montana, New Jersey, Nevada, Oregon, Vermont, and Washington. It is expected that the wave of legalization will continue to the point of some form of federal legalization or decriminalization.

Typically, marijuana products are available to users for purchase in specialized "dispensaries" that offer dried flower, edibles, tinctures, extracts, and the like. In some cases, a unique or unusual chemical profile, or chemotype, is attractive not only for flower sales but also for use in the preparation of extracts and/or isolates and for the manufacture of a variety of products that possess characteristics of the chemotype.

SUMMARY OF THE INVENTION

*C. sativa* cultivar 'OW-1' is a new cultivar which has elevated levels of CBGA. *C. sativa* cultivar 'OW-1' is a tall growing plant. The variety has a strong fragrance at 7 weeks old. The variety has a very low flower to leaf ratio of 6 to 1. The variety grows best with warm days, cool nights, and high nutrient base feeding.

The variety can be used to treat certain medical conditions. For example, the variety can be used to treat rheumatoid arthritis. For example, the variety can be used to treat bowel disorders such as Crohn's Disease.

The new variety is a result of controlled cross of wild Oaxacan (unpatented) and 'Pennywise' (unpatented) in Willow, Alaska, performed in 2012. The new variety differs from the parental wild Oaxacan variety primarily in terms of its terpene profile, such that the new variety has a markedly more floral aroma than the wild Oaxacan variety, whose aroma is characterized by carthy herbs, peppery fruits, and a sour citrus overtone. The new variety differs from the parental 'Pennywise' variety in that it contains a greater percentage of THC, CBGA, and terpenes, and a lower percentage of CBD, as compared with 'Pennywise'. The closest comparison variety is the parental 'Pennywise' variety.

Methods of growing the variety include the use of soil comprising high calcium magnesium. The soil can have a pH of 6.0-6.5.

The variety has been asexually reproduced by vegetative propagation (cloning) from mother plants in Willow, Alaska, beginning in 2013. Asexual reproduction of the new variety has demonstrated that the new variety reproduces true to type with all of the morphological characteristics, as herein described, firmly fixed and retained through successive generations of such asexual propagation.

'OW-1' can have a cannabinoid profile as set forth in Table 1 and a terpene profile as set forth in Table 2. Chemotypic characteristics of each new variety are variable based upon cultivation conditions, as is typical of *Cannabis* plants. Accordingly, while chemotypic information provided herein is representative of performance of the new varieties under a particular set of cultivation conditions, it is not limiting on other chemotypic profiles obtainable under a different set of cultivation conditions. Table 1 and Table 2 provides exemplary profiles as determined by a testing laboratory using methods such as high-performance liquid chromatography (HPLC) and gas chromatography with mass spectrometry. Such tests were performed on harvested material of the new variety after indoor cultivation in Willow, Alaska, where cultivation temperature varied between 56 and 80 degrees F. Due to the natural variability of chemotypic expression that is commonly observed in *Cannabis* plants, arising from numerous causes such as cultivation conditions, the values set forth in the tables do not reflect the only possible range of outcomes that can be obtained from plants of the new variety. Thus, these values are merely exemplary of observed values (middle column) and predicted normal variations from the observed values.

TABLE 1

Exemplary Profiles of Key Cannabinoids.

| | Percent** | Percent | Percent | Percent | Percent |
|---|---|---|---|---|---|
| THCA | 12.54 | 16.90 | 21.80 | 26.16 | 30.52 |
| THC | 0.02 | 0.18 | 0.79 | 1.83 | 1.99 |

TABLE 1-continued

Exemplary Profiles of Key Cannabinoids.

| | Percent** | Percent | Percent | Percent | Percent |
|---|---|---|---|---|---|
| Total THC* | 12.24 | 16.23 | 19.95 | 23.70 | 27.69 |
| THCVA | 0.00 | 0.27 | 0.05 | 0.23 | 0.24 |
| CBGA | 0.00 | 1.90 | 4.20 | 6.15 | 6.99 |
| CBG | 0.07 | 0.17 | 0.52 | 0.71 | 0.81 |
| Total CBD | 0.03 | 0.04 | 0.06 | 0.07 | 0.08 |
| Total Cannabinoid | 15.18 | 20.67 | 27.47 | 32.22 | 37.71 |

*Total THC = (THCA * 0.877) + THC (i.e. delta 9 THC) + delta 8 THC
**Percent = Percent (dry weight of flower)

TABLE 2

Exemplary Profiles of Key Terpenes.

| | Percent | Percent | Percent | Percent | Percent |
|---|---|---|---|---|---|
| Alpha Pinene | 0.04 | 0.06 | 0.11 | 0.31 | 0.33 |
| P Cymene | 0.00 | 0.01 | 0.01 | 0.09 | 0.09 |
| G-Terpinene | 0.01 | 0.02 | 0.03 | 0.04 | 0.05 |
| A-Humulene | 0.00 | 0.02 | 0.13 | 0.25 | 0.28 |
| A-Bisabolol | 0.00 | 0.01 | 0.01 | 0.02 | 0.02 |
| Beta Pinene | 0.07 | 0.09 | 0.13 | 0.18 | 0.21 |
| D3carene | 0.03 | 0.04 | 0.07 | 0.10 | 0.11 |
| Limonene | 0.11 | 0.14 | 0.17 | 0.25 | 0.28 |
| Terpinolene | 0.00 | 0.32 | 0.64 | 1.08 | 1.21 |
| Neroliodol | 0.00 | 0.01 | 0.03 | 0.04 | 0.05 |
| Beta Myrcene | 0.21 | 0.30 | 0.47 | 0.80 | 0.89 |
| A-Terpinene | 0.00 | 0.01 | 0.02 | 0.05 | 0.05 |
| Ocimene | 0.27 | 0.39 | 0.60 | 1.05 | 1.17 |
| Linalool | 0.01 | 0.01 | 0.02 | 0.06 | 0.06 |
| B-Caryophyllene | 0.06 | 0.14 | 0.38 | 0.68 | 0.76 |
| Terpene Total | 0.96 | 1.56 | 3.01 | 4.80 | 5.40 |

**Percent = Percent (dry weight of flower)

BRIEF DESCRIPTION OF PICTURES

The accompanying photographs show the typical appearance of the new variety 'OW-1'. The colors are as nearly true as is reasonably possible in a color representation of this type. Colors in the photographs may differ slightly from the color values cited in the detailed botanical description which accurately describes the colors of the new plant. All color specifications provided herein are based upon the RBG Color Model, which uses numerical representations for color, with three "coordinates" that indicate a value for Red, Blue, and Green, in that order. Color quantification was achieved, where feasible, with a digital color sensor colorimeter. Where use of such colorimeter was not feasible do to exceedingly small size of certain structures, such structures were matched with like color samples, which were then read digitally.

DETAILED BOTANICAL DESCRIPTION

Figure 1:
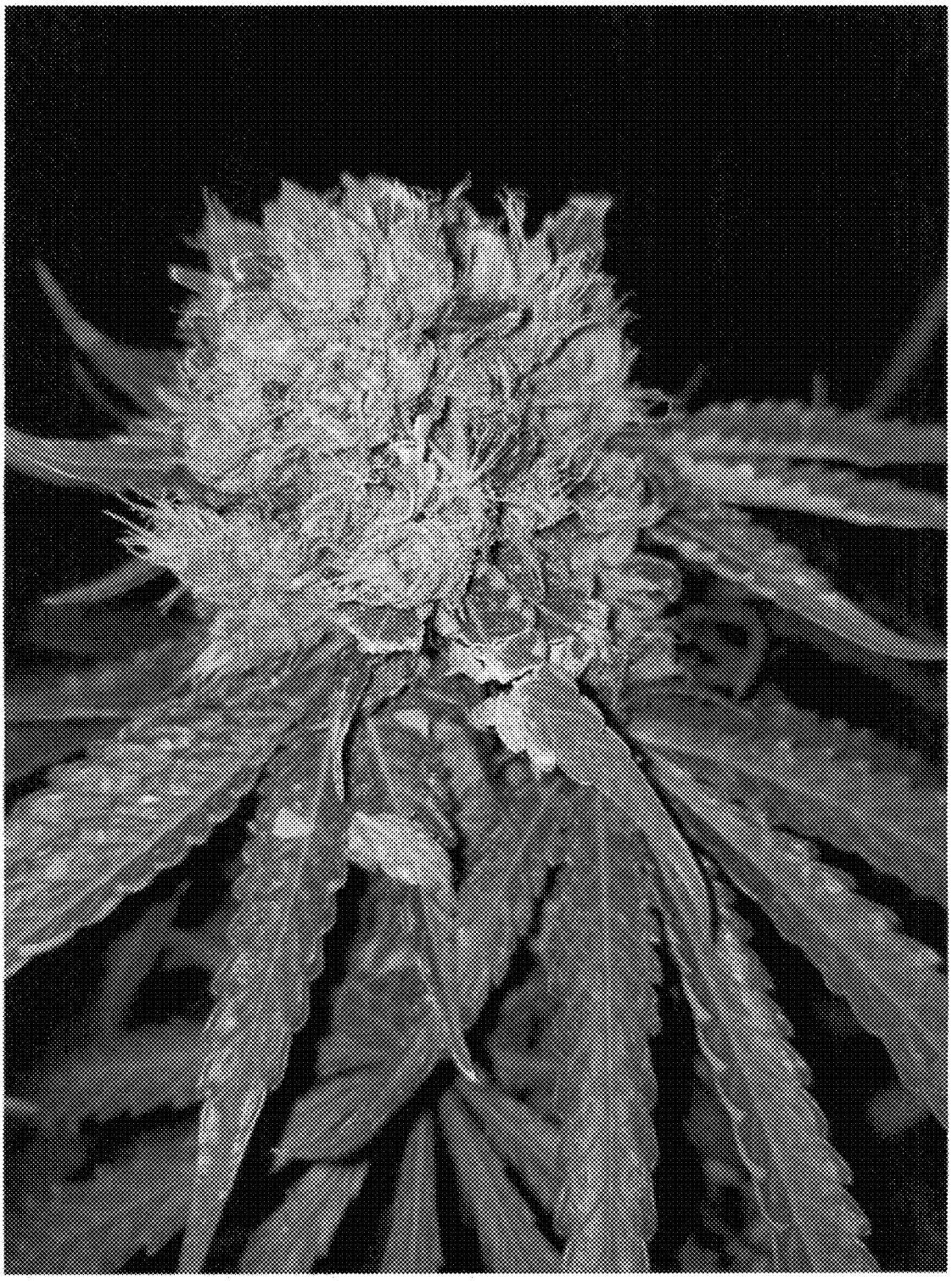
FIG. 1 depicts an inflorescence of 'OW-1' at 7 weeks after induction of flowering, at a total age of 19 weeks after cloning.
Figure 2:
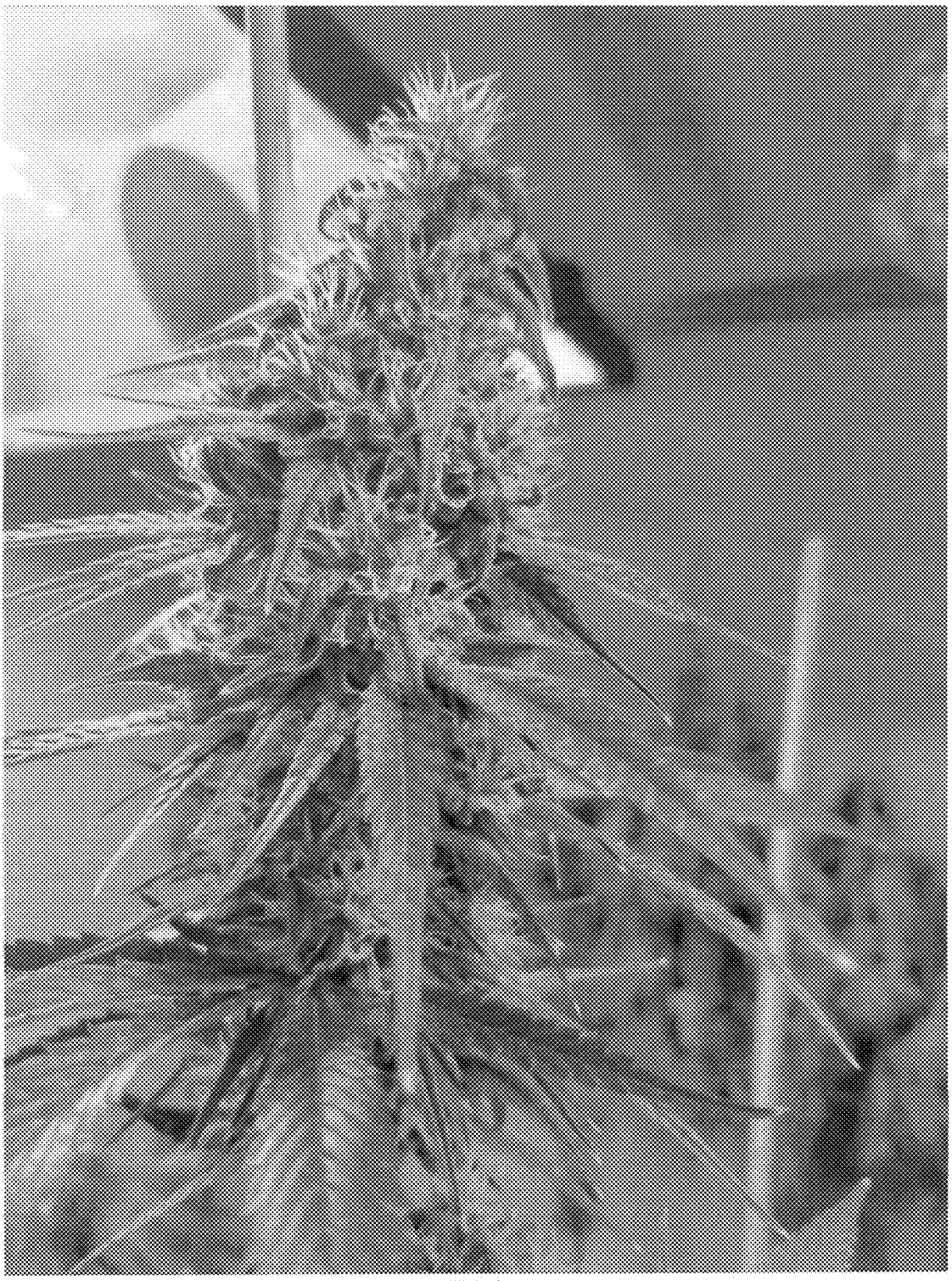
FIG. 2 depicts an inflorescence of 'OW-1' at 7 weeks after induction of flowering, at a total age of 19 weeks after cloning.
Figure 3:
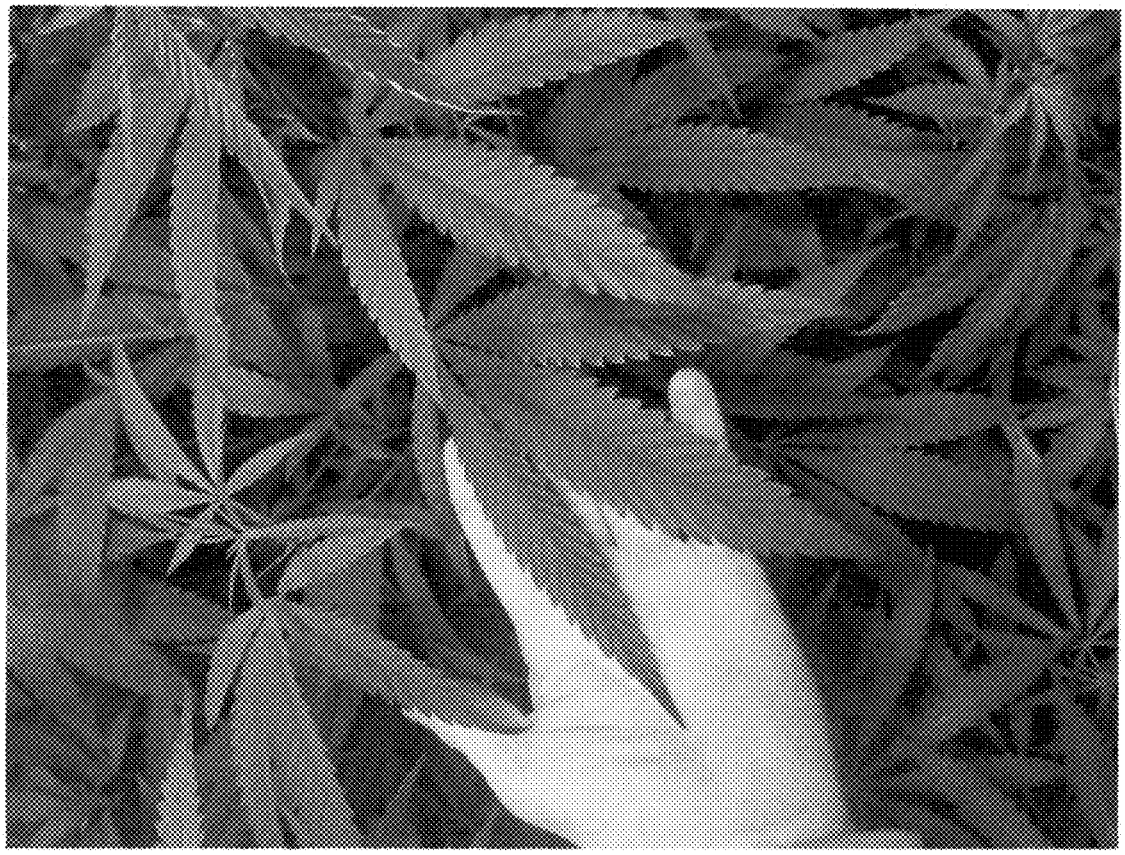
FIG. 3 depicts the leaves of 'OW-1' at 8 weeks of growth under vegetative conditions.
Figure 4:
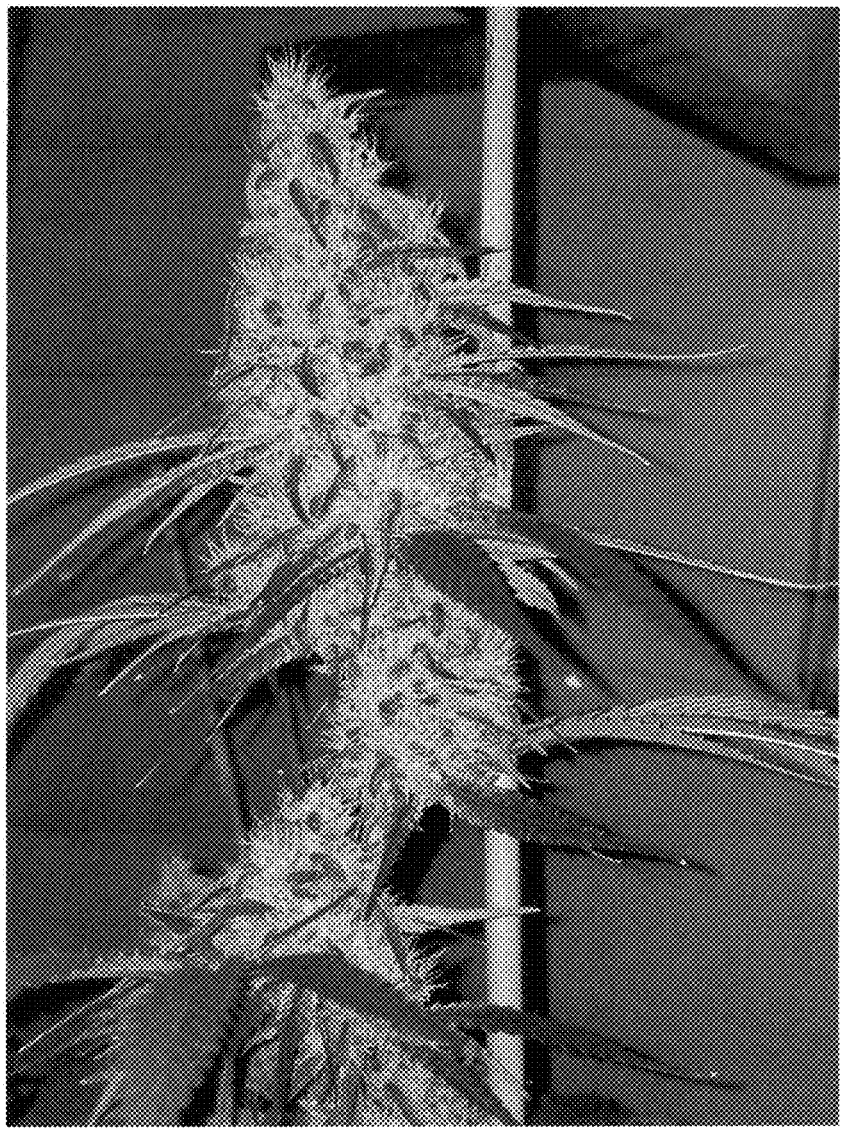
FIG. 4 depicts inflorescence of 'OW-1' at 7 weeks after induction of flowering, at a total age of 19 weeks after cloning.

The following detailed description sets forth the distinctive characteristics of 'OW-1'. The data which define these characteristics were collected from asexual reproductions of the original selection, on plants that were 7 weeks into the flowering stage. Induction of flowering occurs in plants that are in vegetative growth, either by natural changes in daylength or by induction of flowering through changes in lighting of the plants. Ages provided herein are counted from the beginning of the induction of flowering and are typically reported in weeks. Because the duration of vegetative growth can be variable and can be based upon desired plant size, absolute age of plants is less relevant and can be, itself, quite variable. Dimensions, sizes, colors, and other characteristics are approximations and averages set forth as accurately as possible.

Type: Herbaceous tap-rooted annual.

a. *Family*.—Cannabaceae.
b. *Genus*.—*Cannabis*.
c. *Species*.—*sativa*.
d. *Common name*.—Marijuana.

Market class: A medicinal herb intended for use as medical oil, and medicinal herb for sale in *Cannabis* dispensaries and as a home garden plant.

PLANT

General:

a. *Parentage*.—Oaxacan (unpatented) x Pennywise (unpatented).
b. *Growth habit*.—Bushy.
c. *Height*.—6-7 ft.
d. *Spread*.—3 ft.
e. *Growth rate*.—Upon transition from vegetative growth to flowering, plant "stretches" approximately 3× in height and length of main branches.
f. *Cold tolerance*.—50-55° F.
g. *Proportion of hermaphrodite plants*.—Low, none seen in 7 years.
h. *Proportion of female plants*.—100%.
i. *Proportion of male plants*.—0%.

BRANCHES

General:

a. *Branching habit*.—Sporadic at angles (30°).
b. *Primary branch number*.—3 to 6.
c. *Length*.—3 ft.
d. *Diameter*.—½ in.
e. *Texture*.—Rough.
f. *Strength*.—Strong.
g. *Internode length*.—Depends on position in the plant; internodes are longer near the top of the plant; near the bottom of the plant, internodes are about 4 mm; closer to the top of the plant, internodes are about 17-24 mm.
h. *Color*.—Ranges from Green (#849249: 132,146,73) to Violet (#53455B: 83,69,91).

STEMS

General:

a. *Length*.—6 in.
b. *Diameter*.—¼ in.
c. *Texture*.—Rough.
d. *Color*.—Ranges from Green (#849249: 132,146,73) to Violet (#53455B: 83,69,91).

LEAVES

General:

a. *Leaf arrangement*.—1 per flower spot.
b. *Leaf type*.—Large, long tapered leaves.
c. *Number per plant*.—40 to 50.
d. *Length*.—4 in.
e. *Width*.—2½ in.

Leaflets:

a. *Number*.—Typically 5.
b. *Length*.—Depends on age of leaf; outer leaflets are shorter, central leaflet is longest, up to about 13 cm.
c. *Width*.—Central leaflet typically 1.2-1.5 cm in width.
d. *Shape*.—Typical of *Cannabis* leaflets.
e. *Apex*.—Accuminate.
f. *Margin*.—Serrate.
g. *Base*.—Acute.
h. *Texture of upper surface*.—Smooth.
i. *Texture of lower surface*.—Rough.
j. *Color of upper surface*.—#4D6221 — Hue: green.
k. *Color of lower surface*.—#667D3A — Hue: green.
l. *Venation pattern*.—Palmate.
m. *Venation color is similar to color of other parts of upper and lower surface of leaflet. Venation is more notable by structural differences than by color differences.*

PETIOLE

General:

a. *Length*.—Highly variable depending upon age of plant and position of leaf on plant. Average length of petiole at mid-point of mature plant in flowering stage is approximately 4 inches.
b. *Width*.—Highly variable depending upon age of plant and position of leaf on plant. Average width of petiole at mid-point of mature plant in flowering stage is approximately 5 mm.
c. *Texture*.—Smooth.
d. *Color*.—Ranges from Green (#849249: 132,146,73) to Medium Purple (9370DB: 147,112,219).

FLOWER

Inflorescence:

a. *Shape*.—Elongated at upper portions of plant, oval to round on lower and lateral inflorescences.
b. *Length*.—2½ in to 4 in.
c. *Diameter*.—1½ in to 2½ in.
d. *Texture*.—Firm and sticky.
e. *Color*.—Ranges from Golden Foil (#c3c300: 195, 195,0) to Green (#769241: 118,146,65).
f. *Fragrance*.—Intensely floral, characteristic of high amounts of terpinolene and ocimene.
g. *Natural flowering season*.—Depends upon latitude and can be affected by elevation; for outdoor-grown plants, flowering generally begins in August.

Bracts ("sugar leaves" of inflorescence):

a. *Number*.—10 to 20.
b. *Shape*.—Similar in shape to vegetative leaflets.
c. *Length*.—Variable, up to 3 inches.
d. *Width*.—⅓ in.
e. *Apex*.—Accuminate.

f. *Margin*.—Serrate.
g. *Base*.—Acute.
h. *Texture of upper surface*.—Rough — lightly to densely covered in trichomes.
i. *Texture of lower surface*.—Rough — lightly to densely covered in trichomes.
j. *Color of upper surface*.—#4D6221 — Hue: green.
k. *Color of lower surface*.—#667D3A — Hue: green.
l. *Venation pattern*.—Palmate.
m. *Venation color is similar to color of other parts of upper and lower surface of leaflet. Venation is more notable by structural differences than by color differences*.

Stigma:
a. *Number*.—6 to 8 per flower.
b. *Shape*.—Round.
c. *Length*.—⅛ in.
d. *Color*.—Creamy white (#f0e9d6: 240,233,214) to amber (#ffbf00: 255,191,0).

Seeds: None observed.

The invention claimed is:

1. A new and distinct variety of *Cannabis* plant named 'OW-1', as illustrated and described herein.

* * * * *